United States Patent
Fredrick et al.

(10) Patent No.: US 7,108,979 B2
(45) Date of Patent: Sep. 19, 2006

(54) METHODS TO DETECT CROSS-CONTAMINATION BETWEEN SAMPLES CONTACTED WITH A MULTI-ARRAY SUBSTRATE

(75) Inventors: Joseph P. Fredrick, Palo Alto, CA (US); Jacqueline M. Tso, Los Gatos, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 357 days.

(21) Appl. No.: 10/655,430

(22) Filed: Sep. 3, 2003

(65) Prior Publication Data

US 2005/0048505 A1    Mar. 3, 2005

(51) Int. Cl.
*C12Q 1/68* (2006.01)
*C07H 21/02* (2006.01)
*C07H 21/04* (2006.01)

(52) U.S. Cl. .................. 435/6; 536/23.1; 536/24.3
(58) Field of Classification Search .................. 435/6, 435/7.1
See application file for complete search history.

(56) References Cited

U.S. PATENT DOCUMENTS

| | | | |
|---|---|---|---|
| 6,077,674 A | 6/2000 | Schleifer et al. | |
| 6,242,266 B1 | 6/2001 | Schleifer et al. | |
| 6,306,599 B1 | 10/2001 | Perbost | |
| 6,306,643 B1 * | 10/2001 | Gentalen et al. | 435/287.2 |
| 6,309,828 B1 | 10/2001 | Schleifer et al. | |
| 6,319,674 B1 | 11/2001 | Fulcrand et al. | |
| 6,323,043 B1 | 11/2001 | Caren et al. | |
| 6,372,483 B1 | 4/2002 | Schleifer et al. | |
| 6,406,849 B1 | 6/2002 | Dorsel et al. | |
| 6,465,183 B1 | 10/2002 | Wolber | |
| 6,599,693 B1 | 7/2003 | Webb | |
| 6,613,893 B1 | 9/2003 | Webb | |
| 6,770,441 B1 * | 8/2004 | Dickinson et al. | 435/6 |

* cited by examiner

*Primary Examiner*—Ethan Whisenant (57) ABSTRACT

Methods and compositions for detecting cross-contamination between samples contacted with different arrays of a multi-array substrate are provided. The methods involve contacting sample to arrays of a multi-array substrate that contains cross-contamination probes in each of its arrays, and evaluating the resultant sample contacted arrays for cross-contamination between the samples. In many embodiments, the arrays of the multi-array substrate contain a set of cross-contamination probes for a corresponding set of cross-contamination targets in the sample(s). Kits and systems are provided for performing the invention. The subject methods may be used in a variety of different applications, such as gene expression analysis, DNA sequencing, mutation detection, as well as other genomics and proteomics applications.

22 Claims, 2 Drawing Sheets

METHODS TO DETECT CROSS-CONTAMINATION BETWEEN SAMPLES CONTACTED WITH A MULTI-ARRAY SUBSTRATE

FIELD OF THE INVENTION

The field of this invention is arrays, particularly nucleic acid microarrays.

BACKGROUND OF THE INVENTION

In nucleic acid sequencing, mutation detection, proteomics, and gene expression analysis, there is a growing emphasis on the use of high density arrays of immobilized nucleic acid or polypeptide probes. Such arrays can be prepared by a variety of approaches, e.g., by depositing biopolymers, for example, cDNAs, oligonucleotides or polypeptides on a suitable surface, or by using photolithographic techniques to synthesize biopolymers directly on a suitable surface. Arrays constructed in this manner are typically formed in a planar area of between about 4–100 $mm^2$, and can have densities of up to several thousand or more distinct array members per $cm^2$.

In use, an array surface is contacted with a labeled sample containing target analytes (usually nucleic acids or proteins) under conditions that promote specific, high-affinity binding of the analytes in the sample to one or more of the probes present on the array. The goal of this procedure is to quantify the level of binding of one or more probes of the array to labeled analytes in the sample. Typically, the analytes in the sample are labeled with a detectable label such as a fluorescent tag, and quantification of the level of fluorescence associated with a bound probe represents a direct measurement of the level of binding. In turn, this measurement of binding represents an estimate of the abundance of a particular analyte in the sample. A variety of biological and/or chemical compounds may be used as detectable labels in the above-described arrays (See, e.g., Wetmur, J. Crit Rev Biochem and Mol Bio 26:227, 1991; Mansfield et al., Mol Cell Probes. 9:145–56, 1995; Kricka, Ann Clin Biochem. 39:114–29, 2002).

Such arrays are commonly used to perform nucleic acid hybridization assays. Generally, in such a hybridization assay, labeled single-stranded analyte nucleic acid (e.g. polynucleotide target) is hybridized to an immobilized complementary single-stranded nucleic acid probe. Complementary nucleic acid probe binds the labeled target polynucleotide, and the presence of the labeled target polynucleotide of interest is detected and quantified.

Such arrays often contain sectors that may be independently contacted with a sample. These sectors, by virtue of design or by as a consequence of the method by which an array is made, are usually spatially separated from each other, and may be each separately contacted with a different sample in a single hybridization experiment. Such multi-sector arrays are of great use in diagnostic and drug screening applications where one or more samples are incubated with multiple sets of probes, where each set of probes is contained in isolated sectors on the same substrate.

A drawback of strategies that involve contacting more than one sample with a multi-sector array is that cross-contamination may occur between the samples during the time that they are in contact with the array. Sample cross-contamination causes probes contained in one sector of an array to bind targets in the cross-contaminated sample. As a consequence, the data obtained from that sector may be of inferior quality and may not be reliable.

As such, methods of detecting cross-contamination between samples contacted with different sectors of a multi-sector array are needed.

Conventional methods for detecting cross-contamination involve testing of results by binary swapping (i.e., two-way testing) the targets, probes and dye labeling. Such methods, although they are quite effective, are tedious and costly in terms of the number of microarrays used to perform the methods, and the time spent performing the methods and analyzing the results.

As such, there is a need for inexpensive methods of detecting cross-contamination between samples contacted with different sectors of a multi-sector array. This invention meets this, and other, needs.

SUMMARY OF THE INVENTION

Methods and compositions for detecting cross-contamination between samples contacted with different arrays of a multi-array substrate are provided. The methods involve contacting sample to arrays of a multi-array substrate that contains cross-contamination probes in each of its arrays, and evaluating the resultant sample contacted arrays for cross-contamination between the samples. In many embodiments, the arrays of the multi-array substrate contain a set of cross-contamination probes for a corresponding set of cross-contamination targets in the sample(s). Kits and systems are provided for performing the invention. The subject invention finds use in a variety of different applications, including gene expression analysis, DNA sequencing, mutation detection, as well as other genomics and proteomics applications.

DEFINITIONS

Unless defined otherwise, all technical and scientific terms used herein have the same meaning as commonly understood by one of ordinary skill in the art to which this invention belongs. Still, certain elements are defined below for the sake of clarity and ease of reference.

The term "biomolecule" means any organic or biochemical molecule, group or species of interest that may be formed in an array on a substrate surface. Exemplary biomolecules include peptides, proteins, amino acids and nucleic acids.

The term "peptide" as used herein refers to any compound produced by amide formation between a carboxyl group of one amino acid and an amino group of another group.

The term "oligopeptide" as used herein refers to peptides with fewer than about 10 to 20 residues, i.e. amino acid monomeric units.

The term "polypeptide" as used herein refers to peptides with more than 10 to 20 residues.

The term "protein" as used herein refers to polypeptides of specific sequence of more than about 50 residues.

The term "nucleic acid" as used herein means a polymer composed of nucleotides, e.g., deoxyribonucleotides or ribonucleotides, or compounds produced synthetically (e.g. PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions.

The terms "nucleoside" and "nucleotide" are intended to include those moieties that contain not only the known purine and pyrimidine base moieties, but also other heterocyclic base moieties that have been modified. Such modifications include methylated purines or pyrimidines, acylated purines or pyrimidines, or other heterocycles. In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like.

The terms "ribonucleic acid" and "RNA" as used herein refer to a polymer composed of ribonucleotides.

The terms "deoxyribonucleic acid" and "DNA" as used herein mean a polymer composed of deoxyribonucleotides.

The term "oligonucleotide" as used herein denotes single stranded nucleotide multimers of from about 10 to 100 nucleotides and up to 200 nucleotides in length.

The term "polynucleotide" as used herein refers to single or double stranded polymer composed of nucleotide monomers of generally greater than 100 nucleotides in length.

A "biopolymer" is a polymeric biomolecule of one or more types of repeating units. Biopolymers are typically found in biological systems and particularly include polysaccharides (such as carbohydrates), peptides (which term is used to include polypeptides and proteins) and polynucleotides as well as their analogs such as those compounds composed of or containing amino acid analogs or non-amino acid groups, or nucleotide analogs or non-nucleotide groups.

A "biomonomer" references a single unit, which can be linked with the same or other biomonomers to form a biopolymer (e.g., a single amino acid or nucleotide with two linking groups, one or both of which may have removable protecting groups).

An "array," includes any one-dimensional, two-dimensional or substantially two-dimensional (as well as a three-dimensional) arrangement of addressable regions bearing a particular chemical moiety or moieties (such as ligands, e.g., biopolymers such as polynucleotide or oligonucleotide sequences (nucleic acids), polypeptides (e.g., proteins), carbohydrates, lipids, etc.) associated with that region. In the broadest sense, the arrays of many embodiments are arrays of polymeric binding agents, where the polymeric binding agents may be any of: polypeptides, proteins, nucleic acids, polysaccharides, synthetic mimics of such biopolymeric binding agents, etc. In many embodiments of interest, the arrays are arrays of nucleic acids, including oligonucleotides, polynucleotides, cDNAs, mRNAs, synthetic mimics thereof, and the like. Where the arrays are arrays of nucleic acids, the nucleic acids may be covalently attached to the arrays at any point along the nucleic acid chain, but are generally attached at one of their termini (e.g. the 3' or 5' terminus). Sometimes, the arrays are arrays of polypeptides, e.g., proteins or fragments thereof.

Any given substrate may carry one, two, four or more or more arrays disposed on a front surface of the substrate. Depending upon the use, any or all of the arrays may be the same or different from one another and each may contain multiple spots or features. A typical array may contain more than ten, more than one hundred, more than one thousand more ten thousand features, or even more than one hundred thousand features, in an area of less than 20 $cm^2$ or even less than 10 $cm^2$. For example, features may have widths (that is, diameter, for a round spot) in the range from a 10 μm to 1.0 cm. In other embodiments each feature may have a width in the range of 1.0 μm to 1.0 mm, usually 5.0 μm to 500 μm, and more usually 10 μm to 200 μm. Non-round features may have area ranges equivalent to that of circular features with the foregoing width (diameter) ranges. At least some, or all, of the features are of different compositions (for example, when any repeats of each feature composition are excluded the remaining features may account for at least 5%, 10%, or 20% of the total number of features). Interfeature areas will typically (but not essentially) be present which do not carry any polynucleotide (or other biopolymer or chemical moiety of a type of which the features are composed). Such interfeature areas typically will be present where the arrays are formed by processes involving drop deposition of reagents but may not be present when, for example, light directed synthesis fabrication processes are used. It will be appreciated though, that the interfeature areas, when present, could be of various sizes and configurations.

Arrays on the surface of a multi-array substrate are usually independently contactable with sample. In other words, in the absence of any cross-contamination, the arrays may each be separately incubated with sample under conditions suitable for specific binding of targets in the sample with the probes on the arrays. The arrays on the surface of a multi-array substrate are independently contactable with sample because they are spatially distinct, i.e., are physically separated by a distance or structure, that allows different samples to be independently applied to each array of the substrate and then incubated.

Each array may cover an area of less than 100 $cm^2$, or even less than 50 $cm^2$, 10 $cm^2$ or 1 $cm^2$. In many embodiments, the substrate carrying the one or more arrays will be shaped generally as a rectangular solid (although other shapes are possible), having a length of more than 4 mm and less than 1 m, usually more than 4 mm and less than 600 mm, more usually less than 400 mm; a width of more than 4 mm and less than 1 m, usually less than 500 mm and more usually less than 400 mm; and a thickness of more than 0.01 mm and less than 5.0 mm, usually more than 0.1 mm and less than 2 mm and more usually more than 0.2 and less than 1 mm. With arrays that are read by detecting fluorescence, the substrate may be of a material that emits low fluorescence upon illumination with the excitation light. Additionally in this situation, the substrate may be relatively transparent to reduce the absorption of the incident illuminating laser light and subsequent heating if the focused laser beam travels too slowly over a region. For example, substrate 10 may transmit at least 20%, or 50% (or even at least 70%, 90%, or 95%), of the illuminating light incident on the front as may be measured across the entire integrated spectrum of such illuminating light or alternatively at 532 nm or 633 nm.

Arrays can be fabricated using drop deposition from pulsejets of either polynucleotide precursor units (such as monomers) in the case of in situ fabrication, or the previously obtained polynucleotide. Such methods are described in detail in, for example, the previously cited references including U.S. Pat. Nos. 6,242,266, 6,232,072, 6,180,351, 6,171,797, 6,323,043, U.S. patent application Ser. No. 09/302,898 filed Apr. 30, 1999 by Caren et al., and the references cited therein. These references are incorporated herein by reference. Other drop deposition methods can be used for fabrication, as previously described herein.

With respect to methods in which pre-made probes are immobilized on a substrate surface, immobilization of the probe to a suitable substrate may be performed using conventional techniques. See, e.g., Letsinger et al. (1975) *Nucl. Acids Res.* 2:773–786; Pease, A. C. et al., *Proc. Nat. Acad. Sci. USA,* 1994, 91:5022–5026. The surface of a substrate may be treated with an organosilane coupling agent to functionalize the surface. One exemplary organosilane coupling agent is represented by the formula $R_nSiY_{(4-n)}$ wherein: Y represents a hydrolyzable group, e.g., alkoxy, typically lower alkoxy, acyloxy, lower acyloxy, amine, halogen, typically chlorine, or the like; R represents a nonhydrolyzable organic radical that possesses a functionality which enables the coupling agent to bond with organic resins and polymers; and n is 1, 2 or 3, usually 1. One example of such an organosilane coupling agent is 3-glycidoxypropyl-trimethoxysilane ("GOPS"), the coupling chemistry of which is well-known in the art. See, e.g., Arkins, "Silane Coupling Agent Chemistry," *Petrarch Systems Register and Review,* Eds. Anderson et al. (1987). Other examples of organosilane coupling agents are (γ-aminopropyl)triethoxysilane and (γ-aminopropyl)trimethoxysilane. Still other suitable coupling agents are well known to those skilled in the art. Thus, once the organosilane coupling agent has been covalently attached to the support surface, the agent may be derivatized, if necessary, to provide for surface functional groups. In this manner, support surfaces may be coated with functional groups such as amino, carboxyl, hydroxyl, epoxy, aldehyde and the like.

Use of the above-functionalized coatings on a solid support provides a means for selectively attaching probes to the support. For example, an oligonucleotide probe formed as described above may be provided with a 5'-terminal amino group that can be reacted to form an amide bond with a surface carboxyl using carbodiimide coupling agents. 5' attachment of the oligonucleotide may also be effected using surface hydroxyl groups activated with cyanogen bromide to react with 5'-terminal amino groups. 3'-terminal attachment of an oligonucleotide probe may be effected using, for example, a hydroxyl or protected hydroxyl surface functionality.

Also, instead of drop deposition methods, light directed fabrication methods may be used, as are known in the art. Inter-feature areas need not be present particularly when the arrays are made by light directed synthesis protocols.

Where an array includes two more features immobilized on the same surface of a solid support, the array may be referred to as addressable. An array is "addressable" when it has multiple regions of different moieties (e.g., different polynucleotide sequences) such that a region (i.e., a "feature" or "spot" of the array) at a particular predetermined location (i.e., an "address") on the array will detect a particular target or class of targets (although a feature may incidentally detect non-targets of that feature). Array features are typically, but need not be, separated by intervening spaces. In the case of an array, the "target" will be referenced as a moiety in a mobile phase (typically fluid), to be detected by probes ("target probes") which are bound to the substrate at the various regions. However, either of the "target" or "probe" may be the one which is to be evaluated by the other (thus, either one could be an unknown mixture of analytes, e.g., polynucleotides, to be evaluated by binding with the other). Target nucleic acids are found in a sample. The identity of the target nucleotide sequence generally is known to an extent sufficient to allow preparation of various probe sequences hybridizable with the target nucleotide sequence. The term "target sequence" refers to a sequence with which a probe will form a stable hybrid under desired conditions. The target sequence generally contains from about 30 to 5,000 or more nucleotides, preferably about 50 to 1,000 nucleotides. The target nucleotide sequence is generally a fraction of a larger molecule or it may be substantially the entire molecule such as a polynucleotide as described above. The minimum number of nucleotides in the target nucleotide sequence is selected to assure that the presence of a target polynucleotide in a sample is a specific indicator of the presence of polynucleotide in a sample. The maximum number of nucleotides in the target nucleotide sequence is normally governed by several factors: the length of the polynucleotide from which it is derived, the tendency of such polynucleotide to be broken by shearing or other processes during isolation, the efficiency of any procedures required to prepare the sample for analysis (e.g. transcription of a DNA template into RNA) and the efficiency of detection and/or amplification of the target nucleotide sequence, where appropriate.

A "probe" is a biopolymer that is usually immobilized on a substrate, and forms a feature, or element, on an array. Probes, like targets, may be nucleic acids, antibodies, polypeptides, and the like. Nucleic acid probes are hybridizable in that they have a nucleotide sequence that can hybridize to a target nucleic acid, if present, under suitable hybridization conditions. In most embodiments, a probe is a single stranded nucleic acid of at least about 15 bp, at least about 20 bp, at least about 30 bp, at least about 50 bp, at least about 100 bp, at least about 200 bp, at least about 500 bp, at least about 800 bp, at least about 1 kb, at least about 1.6 kb, at least about 2 kb, at least about 3 kb or at least about 5 kb or more in length.

A "scan region" refers to a contiguous (preferably, rectangular) area in which the array spots or features of interest, as defined above, are found. The scan region is that portion of the total area illuminated from which the resulting fluorescence is detected and recorded. For the purposes of this invention, the scan region includes the entire area of the slide scanned in each pass of the lens, between the first feature of interest, and the last feature of interest, even if there exist intervening areas which lack features of interest. An "array layout" refers to one or more characteristics of the features, such as feature positioning on the substrate, one or more feature dimensions, and an indication of a moiety at a given location. "Hybridizing" and "binding", with respect to polynucleotides, are used interchangeably.

The term "substrate" as used herein refers to a surface upon which marker molecules or probes, e.g., an array, may be adhered. Glass slides are the most common substrate for biochips, although fused silica, silicon, plastic and other materials are also suitable.

The term "flexible" is used herein to refer to a structure, e.g., a bottom surface or a cover, that is capable of being bent, folded or similarly manipulated without breakage. For example, a cover is flexible if it is capable of being peeled away from the bottom surface without breakage.

"Flexible" with reference to a substrate or substrate web, references that the substrate can be bent 180 degrees around a roller of less than 1.25 cm in radius. The substrate can be so bent and straightened repeatedly in either direction at least 100 times without failure (for example, cracking) or plastic deformation. This bending must be within the elastic limits of the material. The foregoing test for flexibility is performed at a temperature of 20° C.

A "web" references a long continuous piece of substrate material having a length greater than a width. For example, the web length to width ratio may be at least 5/1, 10/1, 50/1, 100/1, 200/1, or 500/1, or even at least 1000/1.

The substrate may be flexible (such as a flexible web). When the substrate is flexible, it may be of various lengths including at least 1 m, at least 2 m, or at least 5 m (or even at least 10 m).

The term "rigid" is used herein to refer to a structure, e.g., a bottom surface or a cover that does not readily bend without breakage, i.e., the structure is not flexible.

The terms "hybridizing specifically to" and "specific hybridization" and "selectively hybridize to," as used herein refer to the binding, duplexing, or hybridizing of a nucleic acid molecule preferentially to a particular nucleotide sequence under stringent conditions.

The term "stringent conditions" refers to conditions under which a probe will hybridize preferentially to its target subsequence, and to a lesser extent to, or not at all to, other sequences. Put another way, the term "stringent hybridization conditions" as used herein refers to conditions that are compatible to produce duplexes on an array surface between complementary binding members, e.g., between probes and complementary targets in a sample, e.g., duplexes of nucleic acid probes, such as DNA probes, and their corresponding nucleic acid targets that are present in the sample, e.g., their corresponding mRNA analytes present in the sample. A "stringent hybridization" and "stringent hybridization wash conditions" in the context of nucleic acid hybridization (e.g., as in array, Southern or Northern hybridizations) are sequence dependent, and are different under different environmental parameters. Stringent hybridization conditions that can be used to identify nucleic acids within the scope of the invention can include, e.g., hybridization in a buffer comprising 50% formamide, 5×SSC, and 1% SDS at 42° C., or hybridization in a buffer comprising 5×SSC and 1% SDS at 65° C., both with a wash of 0.2×SSC and 0.1% SDS at 65° C. Exemplary stringent hybridization conditions can also include a hybridization in a buffer of 40% formamide, 1 M NaCl, and 1% SDS at 37° C., and a wash in 1×SSC at 45° C. Alternatively, hybridization to filter-bound DNA in 0.5 M $NaHPO_4$, 7% sodium dodecyl sulfate (SDS), 1 mnM EDTA at 65° C., and washing in 0.1×SSC/0.1% SDS at 68° C. can be employed. Yet additional stringent hybridization conditions include hybridization at 60° C. or higher and 3×SSC (450 mM sodium chloride/45 mM sodium citrate) or incubation at 42° C. in a solution containing 30% formamide, 1M NaCl, 0.5% sodium sarcosine, 50 mM MES, pH 6.5. Those of ordinary skill will readily recognize that alternative but comparable hybridization and wash conditions can be utilized to provide conditions of similar stringency.

In certain embodiments, the stringency of the wash conditions that set forth the conditions which determine whether a nucleic acid is specifically hybridized to a probe. Wash conditions used to identify nucleic acids may include, e.g.: a salt concentration of about 0.02 molar at pH 7 and a temperature of at least about 50.° C. or about 55° C. to about 60° C.; or, a salt concentration of about 0.15 M NaCl at 72° C. for about 15 minutes; or, a salt concentration of about 0.2×SSC at a temperature of at least about 50° C. or about 55.° C. to about 60° C. for about 15 to about 20 minutes; or, the hybridization complex is washed twice with a solution with a salt concentration of about 2×SSC containing 0.1% SDS at room temperature for 15 minutes and then washed twice by 0.1×SSC containing 0.1% SDS at 68° C. for 15 minutes; or, equivalent conditions. Stringent conditions for washing can also be, e.g., 0.2×SSC/0.1% SDS at 42° C. In instances wherein the nucleic acid molecules are deoxyoligonucleotides ("oligos"), stringent conditions can include washing in 6×SSC/0.05% sodium pyrophosphate at 37.° C. (for 14-base oligos), 48.° C. (for 17-base oligos), 55° C. (for 20-base oligos), and 60° C. (for 23-base oligos). See Sambrook, Ausubel, or Tijssen (cited below) for detailed descriptions of equivalent hybridization and wash conditions and for reagents and buffers, e.g., SSC buffers and equivalent reagents and conditions.

Stringent hybridization conditions are hybridization conditions that are at least as stringent as the above representative conditions, where conditions are considered to be at least as stringent if they are at least about 80% as stringent, typically at least about 90% as stringent as the above specific stringent conditions. Other stringent hybridization conditions are known in the art and may also be employed, as appropriate.

Two nucleotide sequences are "complementary" to one another when those molecules share base pair organization homology. "Complementary" nucleotide sequences will combine with specificity to form a stable duplex under appropriate hybridization conditions. For instance, two sequences are complementary when a section of a first sequence can bind to a section of a second sequence in an anti-parallel sense wherein the 3'-end of each sequence binds to the 5'-end of the other sequence and each A, T(U), G, and C of one sequence is then aligned with a T(U), A, C, and G, respectively, of the other sequence. RNA sequences can also include complementary G=U or U=G base pairs. Thus, two sequences need not have perfect homology to be "complementary" under the invention, and in most situations two sequences are sufficiently complementary when at least about 85% (preferably at least about 90%, and most preferably at least about 95%) of the nucleotides share base pair organization over a defined length of the molecule.

By "remote location," it is meant a location other than the location at which the array is present and hybridization occurs. For example, a remote location could be another location (e.g., office, lab, etc.) in the same city, another location in a different city, another location in a different state, another location in a different country, etc. As such, when one item is indicated as being "remote" from another, what is meant is that the two items are at least in different rooms or different buildings, and may be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. An array "package" may be the array plus only a substrate on which the array is deposited, although the package may include other features (such as a housing with a chamber). A "chamber" references an enclosed volume (although a chamber may be accessible through one or more ports). It will also be appreciated that throughout the present application, that words such as "top," "upper," and "lower" are used in a relative sense only.

The term "sample" as used herein relates to a material or mixture of materials, typically, although not necessarily, in fluid form, containing one or more components of interest.

A "computer-based system" refers to the hardware means, software means, and data storage means used to analyze the information of the present invention. The minimum hardware of the computer-based systems of the present invention comprises a central processing unit (CPU), input means, output means, and data storage means. A skilled artisan can readily appreciate that any one of the currently available computer-based system are suitable for use in the present invention. The data storage means may comprise any manufacture comprising a recording of the present information as described above, or a memory access means that can access such a manufacture.

To "record" data, programming or other information on a computer readable medium refers to a process for storing information, using any such methods as known in the art. Any convenient data storage structure may be chosen, based on the means used to access the stored information. A variety of data processor programs and formats can be used for storage, e.g. word processing text file, database format, etc.

A "processor" references any hardware and/or software combination that will perform the functions required of it. For example, any processor herein may be a programmable digital microprocessor such as available in the form of a electronic controller, mainframe, server or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic medium or optical disk may carry the programming, and can be read by a suitable reader communicating with each processor at its corresponding station.

"Cross-contamination" between two or more samples is an undesirable mixing of the samples. A cross-contaminated sample may contain about 1%, about 1%–5%, about 5% to about 10%, about 10%–about 20%, about 20% to about 30%, or about 30% to about 50% or more, by volume, of another sample. In many embodiments of the invention, cross-contamination of samples contacted with arrays on a multi-array substrate may occur during the period of contact of the samples with the arrays (i.e., incubation of the samples and the array), however, cross-contamination of samples may also occur during washing of the arrays after the period of contact.

A "cross-contamination probe" is a type of probe that detects cross contamination between samples contacted with different arrays of a substrate. A "set of cross-contamination probes" is one or more (e.g., 1, 2 up to about 4, up to about 8, up to about 10, up to about 12, up to about 24, up to about 36 or up to about 48, up to about 96 or a multiple thereof, e.g. about 384 or more) cross-contamination probes. One set of cross-contamination probes is usually present in each array and may be present in duplicate or more in each array. Probes in a set of cross-contamination probes need not be in the same area of an array, and may be present in any area of the array. In other words, individual probes of the set of cross-contamination probes may be present at different positions of the array and need not be present in the same area.

A "cross-contamination target" is a target that specifically binds to a cross-contamination probe. A "set of cross-contamination targets" is one or more (e.g., 1, 2 up to about 4, up to about 8, up to about 10, up to about 12, up to about 24, up to about 36 or up to about 48, up to about 96 or a multiple thereof, e.g., 384 or more) cross-contamination targets. A cross-contamination target corresponds to a cross-contamination probe if it specifically binds to the probe. Cross-contamination targets may be "spiked" into a sample in that they are added to the sample prior to contacting the sample with an array.

Binding of a probe to a target may be "evaluated". "Evaluated", in this context, means that the presence, absence or level of binding of the probe to the target is determined or assessed. Binding of a probe to a target may be evaluated absolutely, e.g., in the absence of binding data for a target to another probe, or relatively, e.g. relative to binding of the probe or another probe to another target. As such, no numerical figure need be associated with the binding of a target to a probe in order for the binding to be evaluated. Accordingly, evaluation may be qualitative, quantitative or semi-quantitative.

DETAILED DESCRIPTION OF THE INVENTION

Methods and compositions for detecting cross-contamination between samples contacted with different arrays of a multi-array substrate are provided. The methods involve contacting sample to arrays of a multi-array substrate that contains cross-contamination probes in each of its arrays, and evaluating the resultant sample contacted arrays for cross-contamination between the samples. In many embodiments, the arrays of the multi-array substrate contain a set of cross-contamination probes for a corresponding set of cross-contamination targets in the sample(s). Kits and systems are provided for performing the invention. The subject invention finds use in a variety of different applications, including gene expression analysis, DNA sequencing, mutation detection, as well as other genomics and proteomics applications.

Before embodiments of the present invention is described in such detail, however, it is to be understood that this invention is not limited to particular variations set forth and may, of course, vary. Various changes may be made to the invention described and equivalents may be substituted without departing from the true spirit and scope of the invention. In addition, many modifications may be made to adapt a particular situation, material, composition of matter, process, process act(s) or step(s), to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

In further describing embodiments of the subject invention, compositions for use in methods of determining cross contamination are described first, followed by a description of the subject methods. Finally, kits and systems for use in practicing the subject methods are described.

Compositions

The invention provides compositions for detecting cross-contamination between samples contacted with at least two arrays of a multi-array substrate. The compositions, in general, involve a set of cross-contamination probes and a set of cross-contamination targets, each of which will be described separately in greater detail below. These components may be part of a system for detecting contamination between samples, the system characterized by including a substrate having at least two arrays each containing a set of cross-contamination probes, and a set of cross-contamination targets corresponding to the cross-contamination probes.

Cross-Contamination Probes

The invention provides a set of at least one cross-contamination probe for use in the subject methods.

Cross-contamination probes are usually situated in each array of a multi-array substrate and specifically bind to the cross-contamination targets that will be described in detail in the next section. Typically, cross-contamination probes do not detectably hybridize to targets other than cross-contamination targets in a sample. In other words, cross-contamination probes do not bind to analyte targets in a sample, where an analyte target is a target for which an estimate of its abundance in the sample is desirable.

Cross-contamination probes are usually present as a set of cross-contamination probes, where each set of cross-contamination probes comprises at least 1 probe, i.e. 1 or more, 2 or more, about 4 or more, about 6 or more, about 8 or more, about 10 or more, about 12 or more, about 24 or more, about 36 or more, about 48 or more or about 96 or a multiple thereof, e.g., 384 or more different probes. In general, the number of cross-contamination probes in a set, if it is more than one, is equal to, or a multiple of, the number of arrays on the multi-array substrate. Each cross-contamination probe set may be present in duplicate, triplicate, quadruplicate, etc., as needed. In most embodiments, the sets of cross-contamination probes present on each array of a multi-array substrate are identical. In other words, if 8 distinct cross-contamination probes are in a set of cross-contamination probes for one array of a multi-array substrate, the same 8 distinct cross-contamination probes will be present on the other arrays of the multi-array substrate.

Cross-contamination probes may be present at any position on an array, i.e., the individual cross-contamination probes of a set may be each be present at different positions of an array, e.g., random or pre-determined positions of an array, or may be in close proximity to each other, e.g., in a line or row. In certain embodiments, the cross-contamination probes are present at positions of an array at which they are most likely to detect cross-contamination. For example, cross-contamination probes may be present at or near the edges of an array of a substrate, particularly near edges of an array that are proximal to other arrays of the substrate, where cross contamination is more likely to occur.

Suitable cross-contamination probes may be selected, for example, by generating test cross-contamination probes and testing them in silica, e.g., by using BLAST or any other sequence comparison program to determine if the test cross-contamination probe is likely to bind to other sequences, or, for example, by generating test cross-contamination probes and testing them experimentally, e.g., by performing binding assays (for example, hybridization assays) to determine if the probe significantly binds to targets in a chosen sample.

Suitable cross-contamination probes may also be selected if a suitable cross-contamination target has been identified: a suitable cross-contamination probe will normally have a sequence that is complementary to the sequence of a suitable target.

As such, suitable cross-contamination probes may have a known or unknown sequence, or a specific or random sequence, depending on how the cross-contamination probe is selected. Cross-contamination probes typically have a sequence that is not present in, and will not hybridize to, the genome of an organism represented by the non-cross-contamination probes on an array. In other words, in most embodiments, if an array contains probes for genes and gene products of a specific species, e.g., humans, the cross-contamination probes on the array will have a sequence that is not represented in the genome of that species or its gene products. For example, in embodiment where the sample contains targets derived from a human, cross-contamination probes may be from yeast, bacteria or any other organism, or may have any other sequence, such that they will not specifically bind to targets in a sample from humans.

Cross-Contamination Targets

The invention provides a set of at least one cross-contamination target for use in the subject methods.

A cross-contamination target usually specifically binds to a single corresponding cross-contamination probe. Typically, when a cross-contamination target is in a sample, it does not detectably bind to other targets in the sample or to probes other than a corresponding cross-contamination probe.

As with the cross-contamination probes, suitable cross-contamination targets may be selected based on their complementarity to a suitable probe, or by any other means such as the in silica or experimental methods described above for selecting a suitable cross-contamination target. Like cross-contamination probes, cross-contamination targets may have a known or unknown sequence, or a specific or random sequence, depending on how the cross-contamination target is selected. Cross-contamination targets typically have a sequence that is not present in and will not hybridize to the genome of an organism represented by the corresponding non-cross-contamination probes on an array. In other words, in most embodiments, if an array contains probes for genes and gene products of a specific species, e.g., humans, the cross-contamination targets in a sample that is intended to be incubated with the array will have sequences that are not represented in the genome of that species or its products. For example, in embodiments involving samples containing targets from humans, cross-contamination targets may be from yeast, bacteria or any other organism, or may have any other sequence, such that they will not specifically bind to probes for human targets. In most embodiments, cross-contamination targets only bind to cross-contamination probes under stringent conditions.

Cross-contamination targets are usually present as a set of cross-contamination targets, where each set of cross-contamination targets comprises at least 1 target, i.e. 1 or more, 2 or more, about 4 or more, about 6 or more, about 8 or more, about 10 or more, about 12 or more, about 24 or more, about 36 or more, about 48, usually up to about 96 or a multiple thereof, e.g., 384 or more different targets. In general, the number of cross-contamination targets in a set is equal to, or a multiple of, the number of corresponding cross-contamination probes that are present in each array of a multi-array substrate. In other words, if a set of cross-contamination probe for a particular array contains only one cross-contamination probe, the set of cross-contamination targets for the array will also consist of one cross-contamination target that is specific for that cross-contamination probe. Similarly, if a set of cross-contamination probes for one array of a multi-array substrate consists of 8 distinct cross-contamination probes, the set of cross-contamination targets for that array will consist of 8 corresponding cross-contamination targets that each will specifically bind one of the cross-contamination probes.

As discussed above, a set of cross-contamination targets usually corresponds to a set of cross-contamination probes that is present on the surface of each array of a multi-array substrate.

One or more distinguishing (i.e. detectably different) cross-contamination targets of a set cross-contamination targets is usually present in each sample prior to its incubation with an array of a multi-array substrate. The presence of one or more distinguishing cross-contamination targets in a sample distinguishes the sample from all other samples to be contacted with the arrays of the multi-array substrate. In other words, the one or more distinguishing cross-contamination targets in a sample provides a unique designation that is particular and unique to the sample, as compared to the other samples for application to a multi-array substrate. At least one distinguishing cross-contamination target thus provides a signature for the sample, the signature defined by the presence, absence or level of the at least one cross-contamination target.

In many embodiments where more than one (i.e., two or more) targets are present in a cross-contamination target set, the distinguishing cross-contamination targets present in a sample represent only a subset, i.e., a portion, of a set of cross-contamination targets. In these embodiments, the distinguishing cross-contamination targets are distinguishable because different cross-contamination targets are present in each sample. In certain embodiments, therefore, a single cross-contamination target is present in each sample, and this cross-contamination target is different in each of the samples.

In embodiments where there may be only one target present in a cross-contamination target set, the concentration of the cross-contamination target in the samples may be modified such that the concentration of the target is different in each sample. In these embodiments, the cross-contamination target is distinguishable in that the concentration of the cross-contamination target is detectably different in each of the samples to be applied to the arrays of a multi-array substrate.

In other embodiments, cross-contamination targets in different samples may be labeled with distinguishable labels such that the targets, even if they are mixed to together, are independently detectable. In other words, each of the samples to be applied to the arrays of a multi-array substrate may contain an identical cross-contamination target that is labeled such that it is distinguishable from targets in other samples. As such, the targets present in the samples to be applied to an array of a multi-array substrate may, collectively, may be labeled with 2, 3, 4, 5, 6, 7 or 8 or more, usually up to about 10, 12 or 14 or more, usually up to about 20 distinguishable labels, with each target being labeled with a single distinguishable label. In certain embodiments, a single target may be aliquoted and each aliquot labeled with a different distinguishable label in order to provide the distinguishable cross-contamination targets.

Examples of causes of contamination include: errors during transfer of sample from a tube onto an array (e.g., pipetting a sample that is intended to be contacted with one array onto two arrays, or pipetting two samples consecutively without changing or cleaning the pipette dispenser used for transfer), sample leakage from one array of a multi-array substrate to another array of a multi-array substrate after contacting the arrays with samples and during incubation under specific binding conditions, and contamination that occurs during washing of the substrate.

As discussed above, in many embodiments, at least one distinguishing cross-contamination target is present in each sample prior to its incubation with an array of a multi-array substrate. These distinguishing cross-contamination targets identify the samples in which they are present and distinguish the samples from each other. In most embodiments, the at least one distinguishing cross-contamination target is made by varying the concentration of at least one cross-contamination target in a set such that it is not present in some samples but present in others, or at different relative concentrations in each of the different samples.

In a relatively straightforward embodiment, in which there are two samples, a distinguishing cross-contamination target may be present in one sample and not present in the other. Alternatively, there may be two different cross-contamination targets, one present in each of the two samples.

In more complex embodiments where there are, for example, four samples and four arrays each containing at least four cross-contamination probes, the different cross-contamination targets of a set of four cross-contamination targets may be individually present (i.e., in the absence of the other targets) in each of the four samples. Alternatively, if there are four samples and four arrays each containing a single cross-contamination probe, a single cross contamination target may be present in the samples at concentrations, e.g., 0.0, 0.33, 0.67, 1.0 (using arbitrary units of concentration), that are detectably different between each of the samples. In these embodiments, the concentrations may be concentrations relative to a standard, e.g., the highest cross-contamination target concentration used, or the concentration of a control such as the same cross-contamination target that is distinguishably labeled and present at the same level in each sample.

Figure 1:
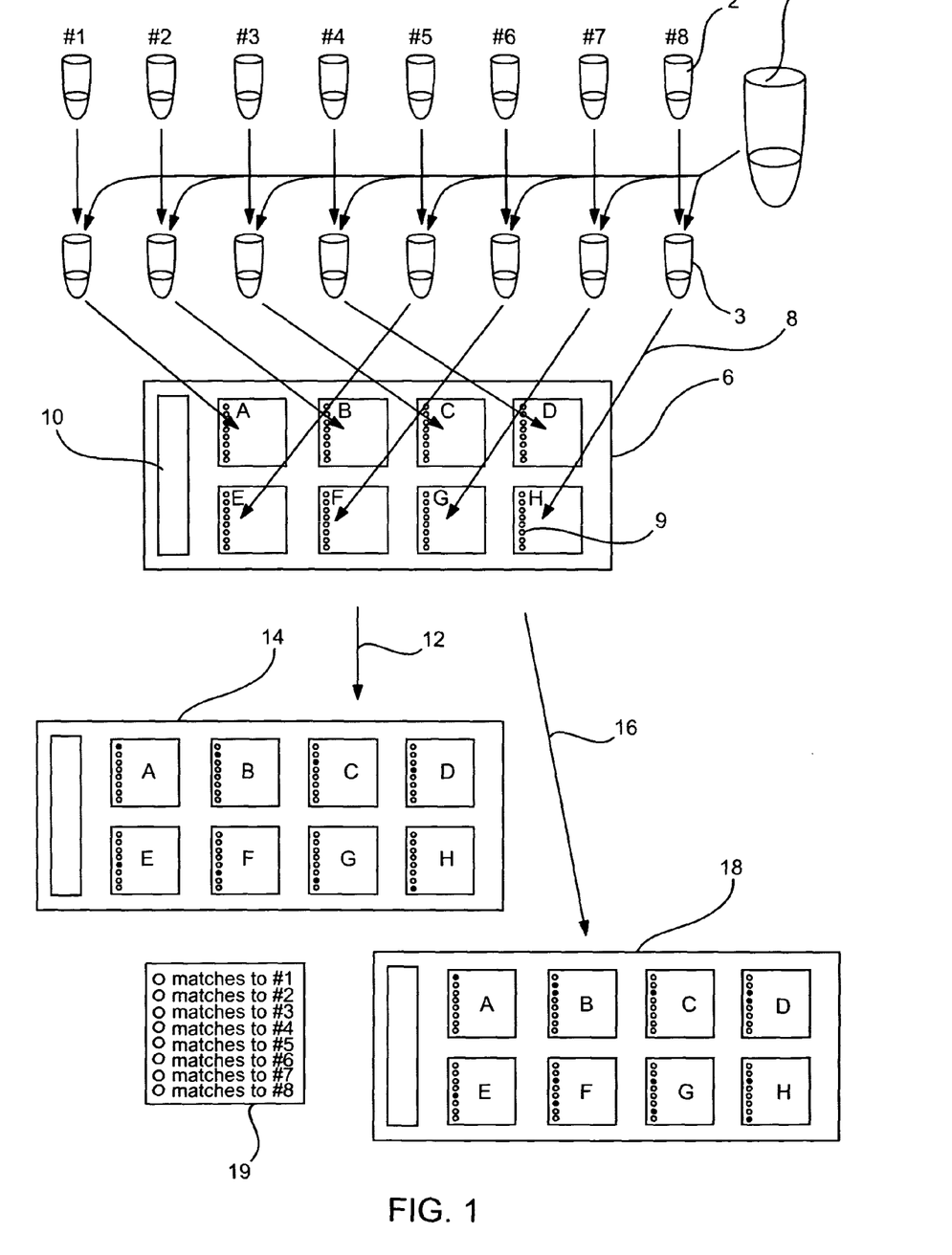
FIG. 1 is a schematic representation of a first exemplary embodiment of the invention.
Figure 2:
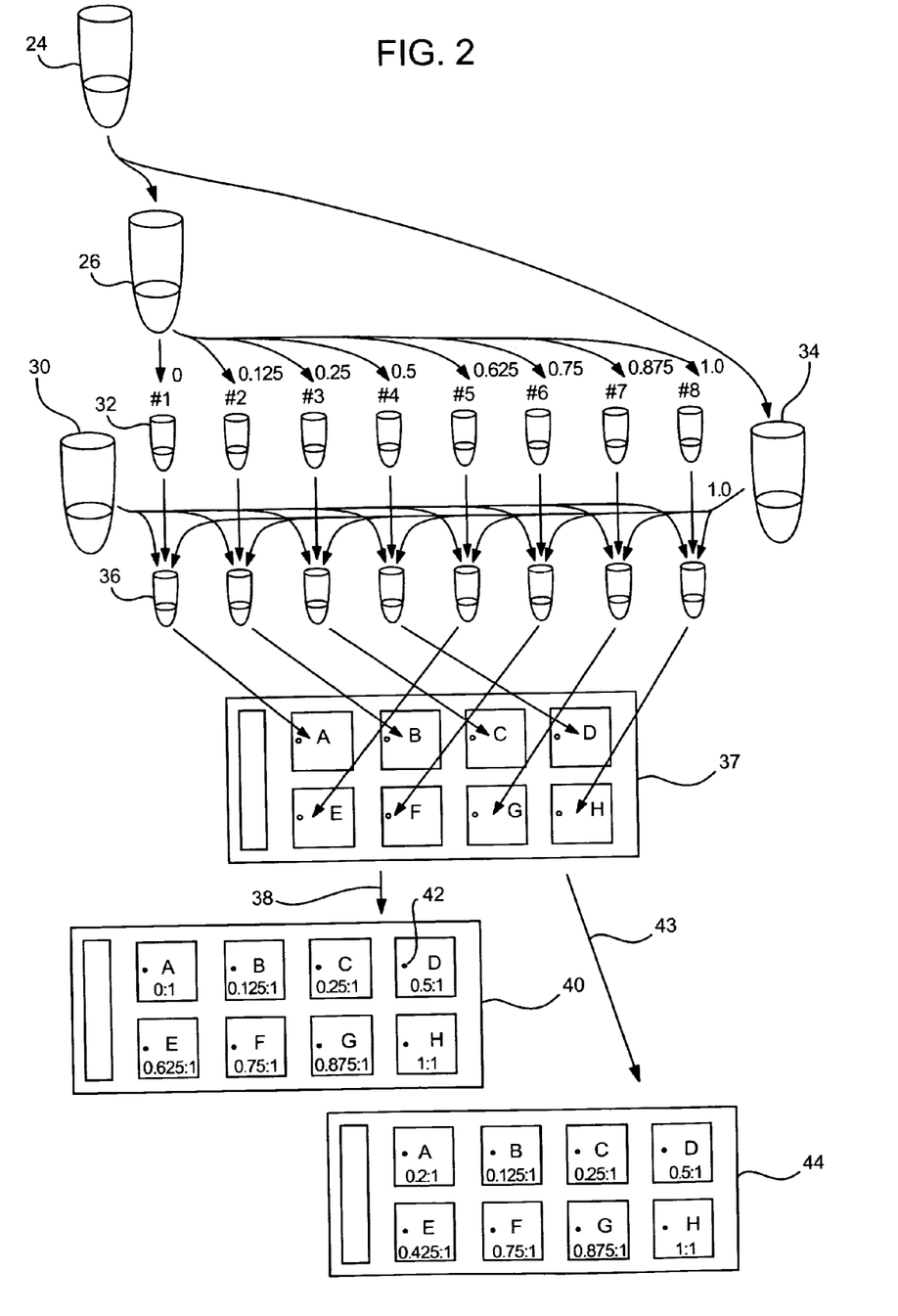
FIG. 2 is a schematic representation of a second exemplary embodiment of the invention.

Illustrated exemplary embodiments of detectably distinguishable sets of probes for eight samples are shown in FIGS. 1 and 2. In the first of these illustrated embodiments (FIG. 1), there are eight cross-contamination targets in the set of eight cross-contamination targets, and each cross-contamination target is present in a different tube separately from the other cross-contamination targets. The tubes containing the eight cross-contamination targets are labeled #1–#8 and are situated at the top of FIG. 1. The tube marked #8 in this series is indicated as 2 in FIG. 1. The eight cross-contamination targets are each individually mixed with different aliquots of a sample (in FIG. 1 the sample is represented by tube 4, however, in practice, the sample may be present in multiple tubes) to make a eight samples containing distinguishing cross-contamination targets (showing as the row of tubes below the set of tubes labeled #1–#8; tube 8 of this row is labeled 3). As such, the individual targets from a set of eight cross-contamination targets are each independently added to samples for eight arrays: each sample contains only one cross-contamination target from the set of eight cross-contamination targets, and that cross-contamination target is a distinguishing cross-contamination target because it is present in only one sample.

In the second of these illustrated embodiments (FIG. 2), a single cross-contamination target in tube 24 is aliquoted into two parts and dispensed into tubes 26 and 34. The cross-contamination target of tube 26 is labeled and diluted to eight different concentrations (0, 0.125, 0.25, etc; in arbitrary concentration units) into tubes #1–#8. The contents of tubes #1–#8 are then each individually mixed with different aliquots of sample 30 (again, in practice, the sample may be present in multiple tubes) to make a eight samples containing distinguishing cross-contamination targets (showing as the row of tubes below the set of tubes labeled #1–#8; tube 1 of this row is labeled 36). In certain embodiments, the cross-contamination target of tube 34 is labeled with a second label that is distinguishable from the label used in tube 26, and the contents of tube 24 are mixed with the samples at the same concentration to provide a control for comparison. As such, the different dilutions of a single cross-contamination target may be independently added to samples for eight arrays: each sample contains only one cross-contamination target at a particular concentration, and since the concentration of that target is distinguishably different in each of the samples, the samples contain distinguishing cross-contamination targets.

In many embodiments, the composition of cross-contamination targets in a sample is known prior to contacting of the sample with an array.

In most embodiments, cross-contamination targets are labeled independently of the rest of the targets of the sample, and are spiked (i.e., added or mixed) into the rest of the sample prior to use. For each set of cross-contamination probes, a single distinguishing cross-contamination target is usually spiked into the rest of the sample prior to use.

For example, cross-contamination targets may be labeled using a T7 RNA amplification labeling procedure and stored, each labeled cross-contamination target in a separate tube. As needed, desired volume (usually about 1–5 µl) of a labeled cross-contamination targets is usually aliquoted the storage tube into a sample tube and mixed with the analyte sample, prior to application of the sample onto an array. Cross-contamination targets may be added to a tube prior to, at the same time as, or after the addition of an analyte sample to a tube.

Cross-contamination targets may be labeled using any known labeling methods. Methods for labeling proteins and nucleic acids are generally well known in the art (e.g. Brumbaugh et al Proc Natl Acad Sci USA 85, 5610–4, 1988; Hughes et al. Nat Biotechnol 19, 342–7, 2001, Eberwine et al Biotechniques. 20:584–91, 1996, Ausubel, et al, Short Protocols in Molecular Biology, 3rd ed., Wiley & Sons, 1995 Sambrook, et al, Molecular Cloning: A Laboratory Manual, Third Edition, 2001 Cold Spring Harbor, N.Y. and DeRisi et al. Science 278:680–686, 1997; Patton W F. Electrophoresis. 2000 21:1123–44; MacBeath G. Nat Genet. 2002 32 Suppl:526–32; and Biotechnol Prog. 1997 13:649–58). These means usually involve either direct chemical modification of the analyte, or a labeled nucleotide that is incorporated into a nucleic acid by nucleic acid replication, e.g., using a polymerase.

Chemical modification methods for labeling a nucleic acid sample usually include incorporation of a reactive nucleotide into a nucleic acid, e.g., an amine-allyl nucleotide derivative such as 5-(3-aminoallyl)-2'-deoxyuridine 5'-triphosphate, using an RNA-dependent or DNA-dependent DNA or RNA polymerase, e.g., reverse transcriptase or T7 RNA polymerase, followed by chemical conjugation of the reactive nucleotide to a label, e.g. a N-hydroxysuccinimdyl of a label such as Cy-3 or Cy5 to make a labeled nucleic acids. Such chemical conjugation methods may be combined with RNA amplification methods, to produce labeled DNA or RNA.

Suitable labels may also be incorporated into a sample by means of nucleic acid replication, where modified nucleotides such as modified deoxynucleotides, ribonucleotides, dideoxynucleotides, etc., or closely related analogues thereof, e.g. a deaza analogue thereof, in which a moiety of the nucleotide, typically the base, has been modified to be bonded to the label. Modified nucleotides are incorporated into a nucleic acid by the actions of a nucleic acid-dependent DNA or RNA polymerases, and a copy of the nucleic acid in the sample is produced that contains the label. Methods of labeling nucleic acids by a variety of methods, e.g., random priming, nick translation, RNA polymerase transcription, etc., are well generally known in the art.

Labels of interest include directly detectable and indirectly detectable radioactive or non-radioactive labels such as fluorescent dyes. Directly detectable labels are those labels that provide a directly detectable signal without interaction with one or more additional chemical agents. Examples of directly detectable labels include fluorescent labels. Indirectly detectable labels are those labels which interact with one or more additional members to provide a detectable signal. In this latter embodiment, the label is a member of a signal producing system that includes two or more chemical agents that work together to provide the detectable signal. Examples of indirectly detectable labels include biotin or digoxigenin, which can be detected by a suitable antibody coupled to a fluorochrome or enzyme, such as alkaline phosphatase. In many preferred embodiments, the label is a directly detectable label. Directly detectable labels of particular interest include fluorescent labels.

Fluorescent labels that find use in the subject invention include a fluorophore moiety. Specific fluorescent dyes of interest include: xanthene dyes, e.g. fluorescein and rhodamine dyes, such as fluorescein isothiocyanate (FITC), 6-carboxyfluorescein (commonly known by the abbreviations FAM and F),6-carboxy-2',4',7',4,7-hexachlorofluorescein (HEX), 6-carboxy-4',5'-dichloro-2',7'-dimethoxyfluorescein (JOE or J), N,N,N',N'-tetramethyl-6-carboxyrhodamine (TAMRA or T), 6-carboxy-X-rhodamine (ROX or R), 5-carboxyrhodamine-6G (R6G$^5$ or G$^5$), 6-carboxyrhodamine-6G (R6G$^6$ or G$^6$), and rhodamine 110; cyanine dyes, e.g. Cy3, Cy5 and Cy7 dyes; coumarins, e.g umbelliferone; benzimide dyes, e.g. Hoechst 33258; phenanthridine dyes, e.g. Texas Red; ethidium dyes; acridine dyes; carbazole dyes; phenoxazine dyes; porphyrin dyes; polymethine dyes, e.g. cyanine dyes such as Cy3, Cy5, etc; BODIPY dyes and quinoline dyes. Specific fluorophores of interest that are commonly used in subject applications include: Pyrene, Coumarin, Diethylaminocoumarin, FAM, Fluorescein Chlorotriazinyl, Fluorescein, R110, Eosin, JOE, R6G, Tetramethylrhodamine, TAMRA, Lissamine, ROX, Napthofluorescein, Texas Red, Napthofluorescein, Cy3, and Cy5, etc.

In certain embodiments, the labels used in the subject methods are distinguishable, meaning that the labels can be independently detected and measured, even when the labels are mixed. In other words, the amounts of label present (e.g., the amount of fluorescence) for each of the labels are separately determinable, even when the labels are co-located (e.g., in the same tube or in the same duplex molecule or in the same feature of an array). Suitable distinguishable fluorescent label pairs useful in the subject methods include Cy-3 and Cy-5 (Amersham Inc., Piscataway, N.J.), Quasar 570 and Quasar 670 (Biosearch Technology, Novato Calif.), Alexafluor555 and Alexafluor647 (Molecular Probes, Eugene, Oreg.), BODIPY V-1002 and BODIPY V1005

(Molecular Probes, Eugene, Oreg.), POPO-3 and TOTO-3 (Molecular Probes, Eugene, Oreg.), and POPRO3 and TOPRO3 (Molecular Probes, Eugene, Oreg.). Further suitable distinguishable detectable labels may be found in Kricka et al. (Ann Clin Biochem. 39:114–29, 2002).

As discussed above, in making a labeled cross-contamination target, it is generally desirable to label the target in a single reaction tube, and then add a portion of the labeled cross-contamination target to the samples prior to their incubation with arrays.

Methods of Detecting Cross-Contamination

These methods described in this section generally employ the afore-mentioned compositions to detect cross-contamination of samples when they are separately contacted with different arrays of a multi-array substrate. In other words, the invention provides a method for determining if a first sample for a first array of a multi-array substrate is contaminated with a second sample for a second array of the substrate. In general, the methods involve: (a) contacting a first array of a multi-array substrate with a first sample under conditions suitable for specific binding of a first distinguishing cross-contamination target in the sample to a first set of at least one cross-contamination probes in the first array; (b) contacting a second array with a second sample under conditions suitable for specific binding of a second distinguishing cross-contamination target to a second set of at least one cross-contamination probes in the second array; and (c) evaluating binding of the second distinguishing cross-contamination target to the first set of at least one cross-contamination probes. In most embodiments, binding of the second distinguishing cross-contamination target to the first set of at least one cross-contamination probes indicates that the first sample is contaminated with the second sample.

Upon preparing samples containing distinguishing cross-contamination targets and contacting each array of a multi-array substrate with a sample, binding of the distinguishing cross-contamination target to the sets of cross-contamination probes on each array is assessed or evaluated. If no cross-contamination occurs, the pattern of binding of the cross-contamination targets to the cross-contamination probe set on each array corresponds to the predicted binding of the distinguishing cross-contamination targets to those probes. If binding of the cross-contamination targets to the cross-contamination probe set on each array does not correspond to the predicted binding of the distinguishing cross-contamination targets to those probes, cross-contamination between samples may have occurred.

In many embodiments, a sample is contacted with a multi-array substrate by transferring, e.g., pipetting, sample from a sample tube directly onto the surface of an array, or, in alternative embodiments, onto an array cover (such as a plastic film or coverslip) that is placed on the array, sample side towards the array. In most embodiments, this process is repeated for each array of a multi-array substrate until a plurality of samples, which may be the same or different, are contacted with the arrays such that one sample is independently contacted with each array.

After incubation of the array under conditions suitable for specific binding of the targets to the probes, the binding of the targets to the probes is assessed. In most embodiments, this involves scanning the array to provide an image of the array, and quantifying the level of binding of the cross-contamination targets to each of the cross-contamination probes. In many embodiments, cross-contamination may be assessed by viewing the image of the array to determine if any unexpected binding of the cross-contamination targets to the cross-contamination probes has occurred. In other embodiments, cross-contamination may be assessed by analysis of any numerical data obtained from the cross-contamination probes. For example, if the data indicate that a particular cross-contamination probe is bound by target at a level that is statistically significant, e.g., above a background level of binding, the sample applied to the array containing that probe may be contaminated.

The following description references the exemplary embodiments illustrated in FIGS. 1 and 2. It is not intended that the invention should be limited to the embodiments showing in these figures. Upon description of the embodiments illustrated in FIGS. 1 and 2, other embodiments that are not specifically described in the figures will become apparent to one of skill in the art FIG. 1 illustrates a method for detecting cross-contamination between samples applied to the eight arrays of a multi-array substrate. The method can be straightforwardly adapted to be used with multi-array substrates with any other number of arrays, e.g., 2, 4, 6, 8 10, 12 or 16 or 24 or 96 or a multiple thereof, e.g., 384, or more arrays.

In the embodiment shown in FIG. 1, as discussed above, eight samples containing distinguishing cross-contamination targets are provided by mixing sample from tube 4 (or any number of tubes containing samples) with different cross-contamination targets from a set of cross-contamination targets provided by the tubes marked #1–#8. The distinguishing cross-contamination targets are represented by the row of tubes underneath the row of tubes labeled #1–#8). Each array a–h of eight-array substrate 6 with optional barcode 10 is contacted 8, under conditions suitable for specific binding between the probes of the array and the targets in the sample, with one of eight samples containing the distinguishing cross-contamination target. After specific binding between the probes of the array and the targets of the sample, binding of the set of eight cross-contamination probes present in each array, e.g. 9, to the set of cross-contamination targets in the samples is determined. Element 19 of FIG. 1 shows an exemplary arrangement of a set of cross-contamination probes in an array: the probes form a row, and each of the eight probes, in order, corresponds to one cross-contamination target. Elements 16 and 18 of FIG. 1 show exemplary results of this method if no cross-contamination 12 or if cross-contamination 18 occurs. Significant binding of the cross-contamination targets to the cross-contamination probes is indicated on elements 14 and 18 using a filled circle, and not significant binding of the cross-contamination targets to the cross-contamination probes is indicated using an open circle.

For a single array, if no cross-contamination occurs, the distinguishing cross-contamination target in the sample applied to the array binds to the cross-contamination probe for that target to provide a pattern of probe binding that corresponds to the distinguishing cross-contamination target in the sample. For example, for a single array, if there is one distinguishing cross-contamination target in the sample applied to that array, there should be significant binding to the cross-contamination probe that corresponds to that target, and no significant binding to the other cross-contamination probes on the array. In other words, if the distinguishing cross-contamination targets are labeled, no cross-contamination is detected if signal from the label is restricted to the cross-contamination probe corresponding to the distinguishing cross-contamination target applied to a particular array. In the embodiment shown in FIG. 1, since a single cross-contamination target is added to each of the samples, the presence of binding to a single cross-contamination probe, corresponding to an expected cross-contamination target (i.e. cross-contamination targets #1–#8), on each array of multi-array substrate 14, indicates that no cross-contamination has occurred.

For a single array, if cross-contamination occurs, the distinguishing cross-contamination target in the sample applied to the array usually binds to the corresponding cross-contamination probe. However, when cross-contamination occurs, a distinguishing cross-contamination probe that was not present in the sample at the time it was applied to the array binds to one of the other cross-contamination probes in the set of cross-contamination probes on the array. Once detected, the binding of a target to a cross-contaminating probe on an array that does not correspond to a particular cross-contamination target present in a sample applied to the array indicates that the sample is cross-contaminated. In other words, if the distinguishing cross-contamination targets in the samples to be applied to the arrays of a multi-array substrate are labeled, cross-contamination is detected if, within an array, label is associated with a cross-contamination probe that does not correspond to distinguishing cross-contamination target present in the sample for that array. As such, an unexpected cross-contamination probe binding pattern indicates the presence of contamination between samples applied to the arrays of a multi-subunit array.

Element 18 of FIG. 1 shows exemplary results of cross-contamination of samples applied to a multi-array substrate. In this example, the sample containing cross-contamination target #3 has contaminated the samples applied to arrays B, F, G, D and H. With reference to element 18, binding of the probes on each array to the corresponding distinguishing cross-contamination targets in each of the samples is observed, however, binding the probe corresponding to cross-contamination target #3 (indicated by the solid circles in each of the arrays), is identified in arrays B, F, G, D and H. Since cross-contamination target #3 was only added to one of the samples applied to this multi-array substrate, and this sample was applied to array C of the multi-array substrate, detection of binding to probes corresponding to cross-contamination target #3 in arrays B, F, G, D and H indicates that the sample containing cross-contamination target #3 contaminated the samples applied to arrays B, F, G, D and H.

As such, this method for detecting cross-contamination not only detects cross-contamination, if present, but also detects the source and amount of the contamination, where the source of the contamination (i.e., the sample from which the contaminating targets are derived). In other words, if a cross-contamination probe/target binding pattern indicates that contamination has occurred, the binding pattern will usually indicate the source and of contamination. For example, if a cross-contamination probe on the first array of a multi-array substrate is bound by a cross-contamination target that was only added to a sample applied to the second array of the substrate, then binding to that probe indicates that cross contamination has occurred, and, that the contaminating sample is the sample applied to the second array of the substrate. Further, by quantifying, at least relatively, the amount of the cross-contamination target in the contaminating sample to the probes on the first and second arrays, the level of binding may be estimated. For example, if an equal amount of target is bound by the probes corresponding to the target, where the probes are on different arrays, the amount of cross-contamination is likely to be high. However, if binding of a cross-contamination target to a probe is barely statistically significant, the amount of cross-contamination is likely to be low.

In the exemplary embodiment shown in FIG. 1, the source of the contamination is the sample containing cross-contamination target #3.

Combined with an assessment of the level of binding of cross-contamination targets to cross-contamination probes, this method of detecting cross-contamination may also quantify the level of cross-contamination. For example, if the level of binding of a certain cross-contamination target to a certain cross-contamination probe is relatively high (e.g., the absolute levels of binding are high relative to control levels of binding, or the levels of binding are similar to binding levels that are known to be high), the level of cross-contamination is also high.

In other embodiments, particularly those in which cross-contamination targets are labeled with distinguishable labels to provide a distinguishing difference between each of the samples to be applied to an multi-array substrate, no cross-contamination is detected if binding of the probes to the targets is as expected, e.g., a single distinguishable label is associated with each of the corresponding cross-contamination probes on each of the arrays of the multi-array substrate. If this is not the case, for example, if a cross-contamination probe on one or more of the arrays of the multi-array substrate is associated with more than one distinguishable label (e.g., two distinguishable labels), cross contamination may have occurred. In an exemplary embodiment, a cross-contamination target is labeled with Cy3 and added to a first sample, and the same cross-contamination target is labeled with Cy5 and added to a second sample. The first sample is applied to a first array of a multi-array substrate and the second sample is added to a second array of the multi-array substrate and incubated under conditions sufficient for binding of the probes to the targets. After washing, the binding patterns of the cross-contamination targets to a cross-contamination probe which is present on both arrays is detected. If the signal associated with the cross-contamination probe on the first array entirely corresponds to a Cy3 signal and the signal associated with the cross-contamination probe on the second array entirely corresponds to a Cy5 signal, then no cross-contamination has occurred. If either of the signals does not entirely correspond to a signal from Cy3 or Cy5 (e.g., a signal corresponds to a signal that corresponds to a mixture of Cy3 and Cy5), then cross-contamination may have occurred.

FIG. 2 illustrates an alternative method for detecting cross-contamination between samples applied to the eight arrays of a multi-array substrate. Again, the method can be straightforwardly adapted to be used with multi-array substrates with any other number of arrays, e.g., 2, 4, 6, 8 10, 12 or 16 or 24 or 96 or a multiple thereof, e.g. 384 or more arrays.

In this exemplary embodiment, as discussed above, eight samples containing distinguishing cross-contamination targets are provided by separating cross-contamination target 24 into two parts 26 and 34, which are labeled using two independently detectable labels (i.e. a pair of labels such as Cy3 and Cy5 which are independently detectable, even if the labels are mixed). The contents of tube 26 (labeled with a first independently detectable label) is aliquoted into tubes #1–#8 such that each tube contains the cross-contamination target at various detectably different concentrations (e.g. 0, 0.125, 0.25, 0.375, etc.). The contents of tube 34, containing the remainder of the split cross-contamination target, is combined with sample from tube 30 (as noted above, any number of tubes may be used to provide target), and added to tubes #1–#8 to make eight samples containing a distinguishing cross-contamination target, as shown by the row of tubes underneath the row of tubes labeled #1–#8, tube 36 being the furthest to the left of these tubes. In this embodiment, an equal amount of the contents of tube 34 is combined with the sample in order to add a constant amount (e.g., 1.0, in arbitrary units) of an independently detectable cross-contamination target to each sample. Results obtained using the cross-contamination targets at various detectably different concentrations are usually compared to results obtained using the independently detectable cross-contamination target to determine if cross-contamination has occurred.

Samples containing the distinguishing cross-contamination targets are contacted with arrays A–H of eight-array substrate 37 under conditions suitable for specific binding between the cross contamination probe of each array (indicated by the open circles on each of arrays A–H) and the cross-contamination target in each sample. After specific binding between the probes of the array and the targets of the samples, binding of the cross-contamination target added to each of the samples to the cross-contamination target on each of the arrays is assessed 38. In most embodiments, using methods that are familiar to one of skill in the art, the binding of the cross-contamination targets at various concentrations to the cross-contamination probe on each array is assessed in first channel (corresponding to its first label), and binding of the internal control cross-contamination target to the cross-contamination probe is assessed in a second channel (corresponding to its distinguishable second label), and numerical figures corresponding to the levels of binding are compared. In most embodiments, the comparison provides a ratio, which, in the embodiments shown in FIG. 2, is a ratio such as 0:1, 0.125:1, 0.25:1, 0.375:1 etc., where the ratio represents the level of binding of a cross-contamination target at certain concentration (the numerator of the ratio) versus the level of binding of the internal control cross-contamination target (the denominator of the ratio). Such ratios could be adequately expressed without the denominator if the denominator is the same for all of the ratios: for example the ratio 0:1, 0.125:1, 0.25:1, 0.375:1, etc., could be expressed as 0, 0.125, 0.25, 0.375, etc. In other words, the level of binding of the cross-contamination target are assessed for each array to provide a normalized numerical values that correspond to the levels of binding of the distinguishing cross-contamination targets to the cross-contamination probe on each array.

Elements 40 and 44 show exemplary results of these methods if no cross-contamination occurs (Element 40) and if cross-contamination occurs (Element 44). If there is no significant cross-contamination 38 between the samples, for a single array, the numerical values of cross-contamination target binding obtained using the above methods corresponds to the concentration of the cross-contamination target added to the sample applied to that array. For example, element 40 shows a multi-array substrate, with eight arrays A–H, each containing a cross-contamination probe 42, bound to a cross-contamination target, if present. The ratios shown in each of the arrays of substrate 40 correspond exactly to the concentration of the cross-contamination target in tubes #1–#8. Such ratios indicate that no significant cross-contamination has occurred. Ratios that do not correspond to the concentration of the cross-contamination target in tubes #1–#8 indicates that cross-contamination has occurred.

In an example of cross contamination 44, where samples applied to arrays A and E are cross-contaminated, the cross-contamination probe/target binding ratios obtained for these arrays is 0.2:1 and 0.425:1. Since 0.2:1 and 0.425:1 does not correspond to the concentrations of the cross-contamination targets added to the samples applied to these arrays (i.e., 0 and 0.125), cross-contamination, e.g., cross-mixing, between the samples applied to arrays A and E is likely to have occurred.

In certain embodiments, sets of identical cross-contamination probes may be placed at a plurality of positions, e.g., about 4 or more, about 8 or more, about 12 or more, about 16 or more, about 20 or more, about 25 or more, about 30 or more, about 40 or more, usually up to about 50 or 100 or more positions, on an array of a multi-array substrate. After applying a sample containing cross-contamination targets for the probes to the array, incubating the sample with the array, and washing the array, the signals associated with the cross-contamination probes may be assessed to determine the degree of binding of the targets to the probes across the array. If the signals are consistent (e.g., they exhibit less than about 30%, less than about 20% less than about 10% or less than about 5% variation) across the array, then a target-detection experiment of high quality may have been performed. However, if significant variation in signals exist (e.g., they exhibit more than about 30%, more than about 50% or more than about 70%) variation, then a problem may have occurred during hybridization. In particular, a gradient of signals (e.g., signals that are strong at one side of an array, signals that are moderate in the middle of the array, and signals that are relatively weak at the other side of the array) indicate a potential problem (e.g. lack of mixing, lack of hybridization uniformity, etc., ), and signals that go abruptly from high to low at a certain position on an array indicate a potential problem (e.g., an air bubble or an incorrectly mounted array cover). Such indications may require further investigation, and may lower the reliability of results obtained from such an experiment. If the moment of cross-contamination occurs during the disassembly and wash steps of the array after hybridization, the gradient of signals may also indicate the directionality of the contamination source (s) in addition to the identity of the contaminating target.

Utility

The methods of this embodiment of the present invention find use in a variety of different applications, where such applications are generally analyte detection applications in which the presence of a particular analyte in a given sample is detected at least qualitatively, if not quantitatively. Protocols for carrying out such assays are well known to those of skill in the art and need not be described in great detail here. Generally, the sample suspected of comprising the analyte of interest is contacted with an array produced according to the methods under conditions sufficient for the analyte to bind to its respective binding pair member that is present on the array. Thus, if the analyte of interest is present in the sample, it binds to the array at the site of its complementary binding member and a complex is formed on the array surface. The presence of this binding complex on the array surface is then detected, e.g., through use of a signal production system, e.g., an isotopic or fluorescent label present on the analyte, etc. The presence of the analyte in the sample is then deduced from the detection of binding complexes on the substrate surface.

Specific analyte detection applications of interest include hybridization assays in which the nucleic acid arrays of the invention are employed. In these assays, at least two samples of target nucleic acids are first prepared, where preparation may include labeling of the target nucleic acids with a label, e.g., a member of signal producing system. Following sample preparation, the samples are contacted with a multi-array substrate under hybridization conditions, whereby complexes are formed between target nucleic acids that are complementary to probe sequences attached to the array surface. The presence of hybridized complexes is then detected. Specific hybridization assays of interest which may be practiced using the arrays include: gene discovery assays, differential gene expression analysis assays; nucleic acid sequencing assays, and the like. Patents and patent applications describing methods of using arrays in various applications include: U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992; the disclosures of which are herein incorporated by reference. The subject methods may be incorporated into an current array assay, as long as method involves separately incubating at least two samples with a corresponding number of arrays on a multi-array substrate.

Where the arrays are arrays of polypeptide binding agents, e.g., protein arrays, specific applications of interest include analyte detection/proteomics applications, including those described in: U.S. Pat. Nos. 4,591,570; 5,171,695; 5,436,170; 5,486,452; 5,532,128; and 6,197,599; the disclosures of which are herein incorporated by reference; as well as published PCT application Nos. WO 99/39210; WO 00/04832; WO 00/04389; WO 00/04390; WO 00/54046; WO 00/63701; WO 01/14425; and WO 01/40803; the disclosures of the United States priority documents of which are herein incorporated by reference.

In certain embodiments, the methods include a step of transmitting data from at least one of the detecting and deriving steps, as described above, to a remote location. By "remote location" is meant a location other than the location at which the array is present and hybridization occur. For example, a remote location could be another location (e.g., office, lab, etc.) in the same city, another location in a different city, another location in a different state, another location in a different country, etc. As such, when one item is indicated as being "remote" from another, what is meant is that the two items are at least in different buildings, and may be at least one mile, ten miles, or at least one hundred miles apart. "Communicating" information means transmitting the data representing that information as electrical signals over a suitable communication channel (for example, a private or public network). "Forwarding" an item refers to any means of getting that item from one location to the next, whether by physically transporting that item or otherwise (where that is possible) and includes, at least in the case of data, physically transporting a medium carrying the data or communicating the data. The data may be transmitted to the remote location for further evaluation and/or use. Any convenient telecommunications means may be employed for transmitting the data, e.g., facsimile, modem, internet, etc.

As such, in using an array made by the method of the present invention, the array will typically be exposed to a sample (for example, a fluorescently labeled analyte, e.g., protein containing sample) and the array then read, following a wash. Reading of the array may be accomplished by illuminating the array and reading the location and intensity of resulting fluorescence at each feature of the array to detect any binding complexes on the surface of the array. For example, a scanner may be used for this purpose which is similar to the AGILENT MICROARRAY SCANNER available from Agilent Technologies, Palo Alto, Calif. Other suitable apparatus and methods are described in U.S. Pat. Nos. 5,091,652; 5,260,578; 5,296,700; 5,324,633; 5,585,639; 5,760,951; 5,763,870; 6,084,991; 6,222,664; 6,284,465; 6,371,370 6,320,196 and 6,355,934; the disclosures of which are herein incorporated by reference. However, arrays may be read by any other method or apparatus than the foregoing, with other reading methods including other optical techniques (for example, detecting chemiluminescent or electroluminescent labels) or electrical techniques (where each feature is provided with an electrode to detect hybridization at that feature in a manner disclosed in U.S. Pat. No. 6,221,583 and elsewhere). Results from the reading may be raw results (such as fluorescence intensity readings for each feature in one or more color channels) or may be processed results such as obtained by rejecting a reading for a feature which is below a predetermined threshold and/or forming conclusions based on the pattern read from the array (such as whether or not a particular target sequence may have been present in the sample). The results of the reading (processed or not) may be forwarded (such as by communication) to a remote location if desired, and received there for further use (such as further processing).

Programming

The invention also provides programming for analysis of array data to determine if cross-contamination has occurred. In general, once the set of cross-contamination probes and targets have been defined for an array and an expected binding pattern to those arrays, in the absence of cross-contamination, has been established, the subject programming may analyze data from the array and determine if unexpected binding of target to the cross-contamination probes has occurred. If cross-contamination has occurred, the programming may, for example, identify or flag data as being unreliable due to cross-contamination.

Such programming may be readily incorporated into any features extraction or any data analysis program. Several commercially available programs perform feature extraction on microarrays, such as IMAGINE® ( by BioDiscovery (Marina Del Rey, Calif.) Stanford University's "ScanAlyze" Software package, Microarray Suite of Scanalytics (Fairfax, Va.), "DeArray" (NIH); PATHWAYS® ( by Research Genetics (Huntsville, Ala.); GEM tools® by Incyte Pharmaceuticals, Inc., (Palo Alto, Calif.); Imaging Research (Amersham Pharmacia Biotech, Inc., Piscataway, N.J.); the RESOLVER® system of Rosetta (Kirkland, Wash.) and the Feature Extraction Software of Agilent Technologies (Palo Alto, Calif.). Such commercially available programs may be adapted or modified to perform the subject methods.

Programming according to the present invention, i.e., programming that allows one to identify cross-contamination as described above, can be recorded on computer readable media, e.g. any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. One of skill in the art can readily appreciate how any of the presently known computer readable mediums can be used to create a manufacture that includes a recording of the present programming/algorithms for carrying out the above described methodology.

Kits

Kits for use in connection with the subject invention may also be provided. Such kits preferably include at least a set of corresponding cross-contamination targets and a set of cross-contamination probes that may, in certain kits, be present on the surface of an array, as discussed above. Kits may also contain instructions for using the kit to detect cross-contamination, if any, of two or more samples using the methods described above.

The instructions are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging), etc. In other embodiments, the instructions are present as an electronic storage data file present on a suitable computer readable storage medium, e.g., CD-ROM, diskette, etc, including the same medium on which the program is presented.

In yet other embodiments, the instructions are not themselves present in the kit, but means for obtaining the instructions from a remote source, e.g. via the Internet, are provided. An example of this embodiment is a kit that includes a web address where the instructions can be viewed from or from where the instructions can be downloaded.

Still further, the kit may be one in which the instructions are obtained are downloaded from a remote source, as in the Internet or world wide web. Some form of access security or identification protocol may be used to limit access to those entitled to use the subject invention. As with the instructions, the means for obtaining the instructions and/or programming is generally recorded on a suitable recording medium.

EXPERIMENTAL

Example 1

In the a first method, N, (where N represents the number of arrays of a multi-array substrate, for exemplary purposes N by be 1, 2, up to about 4, up to about 8, up to about 10, up to about 12, up to about 24, 36, 48, 96 or a multiple thereof, e.g., 384 or more), unique spike-in contamination control targets are individually mixed with the hybridization buffer and target of interest. These N aliquots are then dispensed onto the desired probe arrays and hybridized. The N distinguishing contamination control targets are designed to: not cross-hybridize with the targets of interest, not have homology to the other N−1 contamination control targets or probes of interest. For example, for a substrate of eight arrays, N would be 8 and the target preparation method is shown in FIG. 1.

Each array of the multi-array substrate contains a set of M contamination control probes which are perfect matches to each of the N contamination control targets. M equals N in count, or an integral multiple of N. The multiple occurrences of each M control probes represents replicates. Contamination control probe 1 is a perfect match for contamination control target 1, probe 2 for target 2, etc., up to probe M for target N. If no cross-contamination occurs, the targets should hybridize to the targets in a pattern shown at the bottom of FIG. 1, in element 14, for the case where M=8.

When an array of a multi-array substrate is hybridized, binding of the contamination control probes can be assessed to determine if any cross-contamination occurred during hybridization. In the embodiment shown in FIG. 1, on each array only one contamination control probe should produce a significant signal (the signal is from a labeled contamination target) and the other N−1 contamination control probes should produce no significant signal. If more than one contamination control exhibits an above-noise signal it indicates the presence of, the source of and the amount of contamination. For example, for array 5, contamination probe 5 should produce significant signal and all others non-significant signal. If contamination probe 3 also exhibited some above-noise (i.e., significant) signal it would indicate that sub-array 3 hybridization buffer or target spilled over into sub-array 5, cross contaminating it. Since the spike-in target concentrations are known a priori, one can determine the amount of spill over from the level of signal. The M contamination control probes can also be replicated spatially across the entire array to assess both direction and source of carry-over contamination. The spatial position of control probes, hybridized to uniquely distinguishable control targets as described above, can be positioned near the periphery of the array and in the interior of the array among other non-control probes, to assess hybridization uniformity and hyb-buffer mixing quality.

Example 2

In a second method, a single spike-in contamination control target is prepared (in tube 24) and two-color labeled to provide the contents of tubes 26 and 34. One color (e.g., green; Cy3) is reserved and used as a reference and the other (e.g., red; Cy5) is successively diluted into N aliquots where the spike-in concentration [x] of each aliquot is [x/N]. In other words, for an substrate of eight arrays, N=8, the spike-in control targets would be prepared in the following concentrations: ⅛, ¼, ⅜, ½, ⅝, ¾, ⅞ and 1×. For example, for an array of eight sub-arrays, where N=8, the target preparation is shown in FIG. 2.

Each array of a multi-array substrate contains a single contamination control probe which is a perfect match to the contamination control target. When this array of sub-arrays is hybridized, binding of the contamination control probes can be inspected to determine if any cross-contamination occurred during hybridization. In each array, the contamination control probe intensity level should be proportional to its subarray number. For example, sub-array 6 should exhibit a control probe signal level of ⅝ or 0.75×. If its signal level significantly deviates from 0.75×, it indicates that cross-contamination has occurred. In order to improve the signal to noise level of this method, the Cy3 green labeled control target (reserved above) can be used to normalize the Cy5/Cy3 (red/green ratio) levels since the green labeled target is present in the same concentration in each hybridization buffer mix.

It is evident from the above discussion that the embodiments of the subject invention provide an important breakthrough in the analysis of microarray data. Specifically, they can allow one to detect cross-contamination between two samples contacted with a multi-array substrate. Information regarding cross-contamination may be used to, e.g., remove or label data that is unreliable, giving a researcher confidence that data for a certain array is accurate, etc. In addition, contamination control probes replicated spatially across the entire array can be used to assess both direction and source of carry-over contamination. The spatial position of control probes, hybridized to uniquely distinguishable control targets as described above, positioned near the periphery of the array and in the interior of the array among other non-control probes, can be used to assess hybridization uniformity and hyb-buffer mixing quality. Accordingly, embodiments of the subject invention represents a significant contribution to the art.

All publications and patents cited in this specification are herein incorporated by reference as if each individual publication or patent were specifically and individually indicated to be incorporated by reference. The citation of any publication is for its disclosure prior to the filing date and should not be construed as an admission that the present invention is not entitled to antedate such publication by virtue of prior invention.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method for determining if a first sample for a first array of a multiple array substrate is contaminated with a second sample for a second array of said substrate, said method comprising:
    (a) contacting said first array with said first sample under conditions suitable for specific binding of a first distinguishing cross-contamination target in said sample to a first set of at least one cross-contamination probes in said first array;
    (b) contacting said second array with said second sample under conditions suitable for specific binding of a second distinguishing cross-contamination target to a second set of at least one cross-contamination probes in said second array; and
    (c) evaluating binding of said second distinguishing cross-contamination target to said first set of cross-contamination probes;
    wherein binding of said second distinguishing cross-contamination target to said first set of cross-contamination probes indicates that said first sample is contaminated with said second sample.

2. The method of claim 1, wherein prior to the contacting step (a), said second distinguishing cross-contamination target is spiked into said second sample.

3. The method of claim 1, wherein said first and said second distinguishing cross-contamination targets do not specifically bind to each other and do not specifically bind to the same cross-contamination probe.

4. The method of claim 1, wherein said set of cross-contamination probes in said first array and said set of cross-contamination probes in said second array are identical sets of probes.

5. The method of claim 4, wherein binding of said second distinguishable cross-contamination target to said first set of cross-contamination probes provides a binding pattern that is different from the binding pattern produced by binding of said second distinguishing cross-contamination target to said second set of cross-contamination probes.

6. The method of claim 5, wherein said binding pattern is characterized by the presence or absence of binding of said first and second distinguishing cross-contamination targets to said cross-contamination probes.

7. The method of claim 1, wherein said first and said second distinguishing cross-contamination targets are distinguishing because they contain the same targets at detectably different concentrations.

8. The method of claim 7, wherein said detectably different concentrations are selected from an undetectable concentration and a detectable concentration.

9. The method of claim 1, wherein the number of cross-contamination probes in said set of cross-contamination probes is equal to a number of arrays of said substrate.

10. The method of claim 9, wherein the number of sets of cross-contamination probes is identical to the number of cross-contamination targets in a set of cross-contamination targets.

11. The method of claim 1, wherein said evaluating step (c) includes determining the amount of binding of said second distinguishing cross-contamination target to said set of cross-contamination probes in said first array.

12. The method of claim 11, wherein said determining step comprises detecting the presence or absence of binding of said first distinguishing cross-contamination target to said second set of cross-contamination probes.

13. The method of claim 11, wherein said determining step is determining an absolute or relative amount of binding.

14. The method of claim 12, wherein said relative amount is an amount relative to a control amount of binding.

15. The method of claim 11, wherein a greater than predicted amount of binding of a particular cross-contamination target indicates that contamination has occurred.

16. A method of detecting the presence of an analyte in a sample, said method comprising:
    (a) contacting a sample suspected of containing said analyte with an array comprising probes for said analyte and a set of cross-contamination probes for detecting contamination of said sample; and
    (b) detecting any binding complexes on the surface of the said array to determine the presence of said analyte in said sample and whether said sample is contaminated.

17. The method of claim 16, further comprising determining if cross-contamination has occurred.

18. The method of claim 17, further comprising determining the source of said cross-contamination, if present.

19. The method of claim 16, wherein said analyte is a nucleic acid and said array is an array of nucleic acid probes.

20. A hybridization assay comprising the steps of:
    (a) contacting at least one target nucleic acid sample labeled with a detectable label with a substrate having at least two separate nucleic acid arrays, each array containing a set of cross-contamination probes, to produce a hybridization pattern for said nucleic acid sample; and
    (b) analyzing said hybridization pattern to produce data on the amounts of said target nucleic acid in said sample and determine if cross-contamination has occurred.

21. The method according to claim 20, wherein said method further comprises washing said array prior to said detecting step.

22. A method of detecting contamination of a first sample applied to a first array of a multi-array substrate, comprising:
    evaluating binding of a component that is unique to said first sample to a second array of said multi-array substrate to detect contamination of said first sample.

* * * * *